(12) United States Patent
Norrild et al.

(10) Patent No.: US 7,892,748 B2
(45) Date of Patent: Feb. 22, 2011

(54) REAGENT FOR DETECTING AN ANALYTE

(75) Inventors: Jens Christian Norrild, Birkeroed (DK); Bo Wegge Laursen, Roskilde (DK)

(73) Assignee: Precisense A/S, Horsholm (DK)

( * ) Notice: Subject to any disclaimer, the term of this patent is extended or adjusted under 35 U.S.C. 154(b) by 1025 days.

(21) Appl. No.: 10/582,794

(22) PCT Filed: Dec. 14, 2004

(86) PCT No.: PCT/EP2004/014199

§ 371 (c)(1),
(2), (4) Date: Oct. 31, 2006

(87) PCT Pub. No.: WO2005/059037

PCT Pub. Date: Jun. 30, 2005

(65) Prior Publication Data

US 2007/0148652 A1    Jun. 28, 2007

(30) Foreign Application Priority Data

Dec. 16, 2003   (GB) ................................. 0329161.4

(51) Int. Cl.
*G01N 33/53* (2006.01)
*C09B 11/04* (2006.01)

(52) U.S. Cl. ................. 435/7.1; 435/4; 435/6

(58) Field of Classification Search ............. 435/46, 435/7.1; 552/101
See application file for complete search history.

(56) References Cited

U.S. PATENT DOCUMENTS

| | | | |
|---|---|---|---|
| 4,679,562 A | 7/1987 | Luksha | |
| 5,194,393 A | 3/1993 | Hugl et al. | |
| 5,277,872 A | 1/1994 | Bankert et al. | |
| 5,342,789 A | 8/1994 | Chick et al. | |
| 5,476,776 A | 12/1995 | Wilkins | |
| 6,002,954 A | 12/1999 | Van Antwerp et al. | |
| 6,256,522 B1 | 7/2001 | Schultz | |
| 6,485,703 B1* | 11/2002 | Cote et al. | 424/9.1 |
| 6,927,246 B2 | 8/2005 | Noronha et al. | |
| 7,045,361 B2 | 5/2006 | Heiss et al. | |
| 7,297,548 B2 | 11/2007 | Kawanishi et al. | |
| 2002/0102267 A1* | 8/2002 | Lu et al. | 424/185.1 |
| 2003/0166028 A1* | 9/2003 | Burroughs-Tencza | 435/7.32 |
| 2004/0259206 A1* | 12/2004 | Thurmond et al. | 435/69.1 |

FOREIGN PATENT DOCUMENTS

| | | |
|---|---|---|
| EP | 0 805 190 A2 | 11/1997 |
| EP | 0 940 450 | 9/1999 |
| EP | 1 188 760 A1 | 3/2002 |
| JP | H10-088124 | 4/1998 |
| JP | 2000-184894 | 7/2000 |
| WO | 89/09833 | 10/1989 |
| WO | 99/16832 | 4/1999 |
| WO | 00/58406 | 10/2000 |
| WO | WO 00/75150 A1 | 12/2000 |
| WO | 02/30275 | 4/2002 |

OTHER PUBLICATIONS

STN Regsitry prinout for Crystal Violet downloaded May 9, 2010.*
Aldrich Catalog (1996) p. 1352.*
Owen et al. J. Appl. Chem. Biotechnol. (1972) 22(10): 1043-1052.*
Whitson et al. Analytical Biochemistry (2004; available on-line Nov. 27, 2003) 324: 227-236.*
STN Regsitry prinout for Alexa Flour 594 downloaded May 9, 2010.*
International Search Report for PCT/EP04/14199 dated Jun. 1, 2005.
Rolinkski et al, "A time-resolved near-infrared fluorescence assay for glucose: opportunities for trans-dermal sensing", J. Photochem. Photobiol. B: Biol. 54 (2000) 26-34.
Laursen et al., *2,6,10-Tris(dialkylamino)trioxatriangulenium Ions. Synthesis, Structure, and Properties of Exceptionally Stable Carbenium Ions*, JACS, vol. 120, No. 47, 1998, XP002328560.
Laursen et al., *Synthesis of a Triazatriangulenium Salt*, Angewandte Chemie, vol. 112, No. 19, Sep. 26, 2000, pp. 3574-3576; XP002328561.
Laursen et al, *Synthesis, Structure and Properties of Azatriangulenium Salts*, Chemistry a European Journal, vol. 7, No. 8, Mar. 23, 2001, pp. 1773-1783, XP002328562.
Lakowicz et al, "Optical Sensing of glucose using phase-modulation fluorimetry", Analytica Chemica Acta, 1993, vol. 271, No. 1, pp. 155-164.

* cited by examiner

*Primary Examiner*—Irene Marx
*Assistant Examiner*—Susan Hanley
(74) *Attorney, Agent, or Firm*—Nixon & Vanderhye P.C.

(57) ABSTRACT

A reagent for use in detecting an analyte comprises a fluorescent energy donor and an energy acceptor, wherein the energy acceptor is of the general formula:

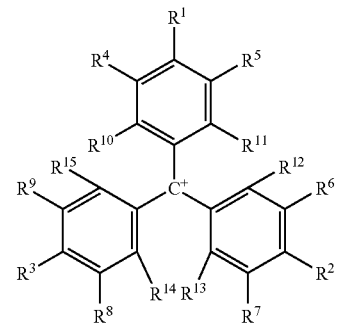

and wherein the distance between the energy donor and the energy acceptor of the reagent is capable of modulation by a suitable analyte to be detected.

33 Claims, 2 Drawing Sheets

REAGENT FOR DETECTING AN ANALYTE

This application is the U.S. national phase of international application PCT/EP2004/014199 filed 14 Dec. 2004, which designated the U.S. and claims benefit of GB 0329161.4 filed 16 Dec. 2003, the entire contents of each of which are hereby incorporated by reference.

The present invention relates to a reagent for use in detecting an analyte, to a dye compound suitable for use in such a reagent, to a method of detecting or measuring an analyte using such a reagent and to a complex of an analyte and such a reagent.

The method of detecting or measuring an analyte relies on FRET (fluorescence resonance energy transfer).

FRET is a distance-dependent interaction between the electronic excited states of two dye species in which excitation energy is transferred from a donor to an acceptor without emission of a photon.

The efficiency of FRET is inversely dependent on the sixth power of the intermolecular separation. [Refs. 1. B. Wieb Van der Meer, G. Coker III, S.-Y. Simon Chen, *Resonance energy transfer; Theory and data*, VCH publishers, 1994; 2. *Principles of Fluorescence Spectroscopy*, Joseph R. Lakowicz (Ed.), 2. edition, Plenum Press, New York 1999]. Detection of FRET can therefore be used to determine the distance between a species labelled with the donor and a species labelled with the acceptor. This may be used for example to determine whether the two species are bound to one another.

The requirements for FRET are:

Donor and acceptor must be in close proximity (typically 10-100 Å)

The absorption spectrum of the acceptor must overlap the fluorescence emission spectrum of the donor.

Donor and acceptor transition dipole orientations must be approximately parallel.

FRET causes a decrease in intensity and lifetime of donor fluorescence. If the acceptor is fluorescent, FRET may also cause an increase in intensity of acceptor fluorescence. Where the donor and acceptor are the same, FRET causes fluorescence depolarization.

FRET may be detected by illuminating a sample with light in the absorption spectrum of the donor and measuring any of these properties.

A simple FRET assay may be carried out by labelling an analyte with a donor and labelling an analyte binding agent with an acceptor (or vice versa). When the analyte is not bound to the analyte binding agent, the distance between the donor and acceptor is large and no FRET occurs.

When the analyte is bound to the analyte binding agent, the distance between the donor and acceptor is small and FRET occurs.

Therefore, detection of FRET may be used to determine whether analyte is present and/or analyte concentration.

A competitive FRET assay may be carried out where labelled analyte competes with non-labelled analyte. In this case, as the concentration of non-labelled analyte increases, there will be less bound labelled analyte. This means that less FRET will occur.

Therefore, again detection of FRET may be used to determine analyte concentration.

An assay of this type may be used for the measurement of glucose concentration. Glucose binds reversibly to a class of proteins called lectins. Concanavalin A is an example of a lectin. The components of the assay are for example labelled concanavalin A (the analyte binding reagent) and labeled glucose or labelled glucose analogue. Dextran is a suitable glucose analogue. When glucose (the analyte) binds to concanavalin A, it displaces labelled glucose or dextran, and less FRET will occur.

Alternatively, the donor and acceptor may be attached to the same species to form a single FRET reagent. An example of such a reagent is a "molecular beacon".

A molecular beacon consists of a single stranded polynucleotide or polynucleotide analogue sequence with a donor attached to one end of the sequence. A complementary acceptor is attached to the other end of the sequence.

The unbound molecular beacon exists as a stem-and-loop structure. The sequences at the ends of the molecular beacon match and bind, creating the stem, while the rest of the probe is unmatched and unbound, creating the loop. While folded this way, the donor at one end of the probe is next to the acceptor at the other end. The proximity of the donor and acceptor allows FRET to occur.

When the probe recognizes and binds to a target, the molecular beacon structure unfolds. This separates the acceptor from the donor so that FRET cannot take place.

Therefore, FRET may be used to determine whether a particular target is present.

Molecular beacons may be used to detect complementary single stranded polynucleotide sequences. Alternatively, they may be used to detect other non-nucleotide species. Such molecular beacons are called aptamers. For example, aptamers may be used to detect proteins.

The molecular beacon has the potential disadvantage that it relies on FRET occurring while the beacon is unbound. During an in vivo assay the beacon sequence may be cleaved by enzymes in the body. This will reduce the FRET. The reduction in FRET caused by beacon degradation cannot be distinguished from the reduction in FRET caused by beacon binding to the target, and the results obtained may therefore be unreliable.

An alternative to a molecular beacon which deals with this problem is a dual probe. This comprises two single stranded polynucleotide or polynucleotide analogue sequences, one labelled with an energy donor and one with a complementary energy acceptor. The dual probe is used to detect a single stranded polynucleotide target sequence which is complementary to the sequences of both parts of the dual probe. When the parts of the dual probe are both bound to the target, FRET occurs. Since FRET does not occur when the dual probe is unbound, dual probe degradation will not affect the occurrence of FRET. Therefore, degradation will not cause the results to be unreliable.

Reagents similar to molecular beacons can be formed from polypeptides.

FRET can also be used in immunoassays.

The choice of donor and acceptor used in FRET is important, and the following factors need to be taken into account.

The donor should have a high quantum yield.

A suitable acceptor must have an absorption spectrum overlapping the emission spectrum of the donor. For example, QSY 21™ is a suitable donor for use with ALEXA FLUOR 21™. It is desirable for an acceptor to have a wide absorption spectrum so that it can be used with a variety of donors.

If the acceptor is also a fluorescent species it is possible that background fluorescence resulting from direct acceptor excitation will occur and be detected as well as donor fluorescence. Filtering of the acceptor emission may result in loss of the donor fluorescence signal where filtering is not sharp enough. Non-fluorescent acceptors such as dabcyl and QSY™ can be used to avoid this problem. Alternatively, the problem can be avoided by choosing an acceptor whose emission spectrum is remote from that of the donor.

The emission spectrum of some donors and absorption spectrum of some acceptors (for example QSY 21™) are shifted when the donor or acceptor is conjugated to an analyte or analyte binding agent. This is undesirable.

Where FRET assays are to be used in vivo, it is desirable for donors to fluoresce at 550 to around 600 nm and for acceptors to absorb light at around 650 nm. This avoids overlap between the donor fluorescence and in vivo autofluorescence at lower wavelengths. Fluorescein fluoresces at 495 nm and is therefore not ideal for in vivo use.

ALEXA FLUOR 594™ is a dye with a suitable emission spectrum for use in vivo. This dye absorbs at 594 nm and fluoresces at 620 nm.

The present inventors have now provided a new class of acceptors (HMCV dyes) for use in FRET. The acceptors are stabilized carbenium ions which are structurally related to crystal violet and malachite green. The acceptors can be derived from intermediates in the synthesis of trioxatriangulenium systems described in Bo W. Laursen et al., J. Am. Chem. Soc., 1998, 120, 12255-12263.

Accordingly, the present invention provides in a first aspect a reagent for use in detecting an analyte, comprising a fluorescent energy donor and an energy acceptor, the energy donor and the energy acceptor being such that when they are sufficiently close to one another energy is non-radiatively transferred from the energy donor following excitation thereof to the energy acceptor quenching fluorescence of the energy donor, wherein the energy acceptor is of the general formula:

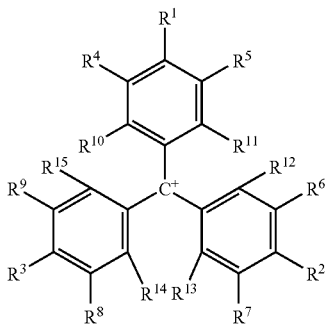

wherein:

$R^1$, $R^2$ and $R^3$ are each independently H, electron donating substituents, or electron withdrawing substituents or $R^3$ is attached to a linker structure, provided that at least two of $R^1$, $R^2$ and $R^3$ are electron donating groups;

$R^4$, $R^5$, $R^6$, $R^7$, $R^8$ and $R^9$ are each independently H, halogen, alkyl, aryl, O-alkyl, S-alkyl and $R^{10}$, $R^{11}$, $R^{12}$, $R^{13}$, $R^{14}$ and $R^{15}$ are each independently hydrogen, O-alkyl, S-alkyl, alkyl, or one or more pairs of groups $R^1$ and $R^4$ and/or $R^1$ and $R^5$ and/or $R^2$ and $R^6$ and/or $R^2$ and $R^7$ and/or $R^3$ and $R^8$ and/or $R^3$ and $R^9$ and/or $R^4$ and $R^{10}$ and/or $R^5$ and $R^{11}$ and/or $R^6$ and $R^{12}$ and/or $R^7$ and $R^{13}$ and/or $R^8$ and $R^{14}$ and/or $R^9$ and $R^{15}$ is a bridging group consisting of aryl, alkylene, O-alkylene, S-alkylene or N-alkylene optionally substituted with one or more of $SO_3^-$, $PO_3^{2-}$, OH, O-alkyl, SH, S-alkyl, COOH, COO$^-$, ester, amide, halogen, SO-alkyl, $SO_2$-alkyl, $SO_2NH_2$, $SO_2NH$-alkyl, $SO_2N$-dialkyl, $SO_3$-alkyl, CN, secondary amine or tertiary amine, provided that not all of $R^{10}$, $R^{11}$, $R^{12}$, $R^{13}$, $R^{14}$ and $R^{15}$ are hydrogen;

and wherein the distance between the energy donor and the energy acceptor of the reagent is capable of modulation by a suitable analyte to be detected.

As used herein, the term "electron donating substituent" includes but is not limited to amino, primary amine, secondary amine, alkyl, O-alkyl, S-alkyl, amide (NHCOR), ester (OCOR), OH, SH and electron rich aryl.

As used herein, the term "electron withdrawing substituent" includes but is not limited to NO, $NO_2$, CN, COOH, ester (COOR), COO$^-$, amide ($CONR_2$), CHO, keto (COR), SO-alkyl, $SO_2$-alkyl, $SO_2NH_2$, $SO_2NH$-alkyl, $SO_2N$-dialkyl, $SO_3$-alkyl, and electron deficient aryl.

Electron rich/deficient aryls may be defined as aryls having electron-donating or -withdrawing substituents respectively.

As used herein, the term "alkyl" and "alkylene" include linear, branched and cyclic groups, saturated and unsaturated groups (including groups containing triple bonds), groups containing one or more substituents, and groups containing one or more heteroatoms. $C_1$ to $C_6$ alkyl groups are preferred.

As used herein, the term "O-alkylene", "N-alkylene" and "S-alkylene" each include groups wherein the heteroatom is at any position within the group. $C_1$ to $C_7$ O-alkylene, N-alkylene and S-alkylene and $C_2$ to $C_7$ alkylene are preferred.

Where an ester substituent is referred to, the substituent may be linked via the carbonyl portion (as R(C=O)OR) or via the alkoxy portion (as RO(C=O)R). Similarly, where an amide substituent is referred to, the substituent may be linked via the carbonyl portion (as $RCONR_2$) or the nitrogen portion (as R(NR)COR).

In one preferred embodiment, the energy donor and energy acceptor are linked together by non-covalent binding. The non-covalent binding may exist between an analyte binding agent linked to one of the energy donor and the energy acceptor and an analyte analogue linked to the other of the energy donor and the energy acceptor, the non-covalent binding being disruptable by a suitable analyte so as to increase the distance between the energy donor and the energy acceptor of the reagent.

Suitably, in this embodiment the analyte binding agent is a lectin and/or the analyte analogue is a glucose analogue. For example, the analyte analogue may be dextran. This system can be used for glucose detection and/or measurement as discussed above.

It is preferable for the lectin to be bound to the energy donor and the analyte analogue to be bound to the energy acceptor (e.g. Dextran-HMCV and Concanavalin A ALEXA FLUOR 594™). Dextran can be more heavily labelled than Concanavalin A. If dextran is labelled with a fluorophore there will be excess fluorescence which dilutes the signal in a lifetime based assay.

In an alternative embodiment, the energy donor and energy acceptor are linked together by a covalent linkage. The covalent linkage between the energy donor and energy acceptor may be cleavable to increase the distance between the energy donor and the energy acceptor of the reagent. Suitably, the energy donor and energy acceptor are linked via a polynucleotide sequence or a polynucleotide analogue sequence or a polypeptide sequence, the sequence having a conformation which is capable of modulation by a suitable analyte to be detected so as to modulate the distance between the energy donor and the energy acceptor of the reagent. In this case, the reagent is a "molecular beacon" as discussed above.

In a further alternative embodiment, the energy donor and the energy acceptor are not linked in the absence of analyte. This reagent may be the "dual probe" discussed above.

Preferably, a linker structure is attached to the energy acceptor at $R^3$, or where a bridging group is present optionally the linker structure is attached to the energy donor at the bridging group.

Preferably, the electron donating substituents are selected from amino, primary amine, secondary amine, O-alkyl, alkyl, S-alkyl, amide, ester, OH and SH.

Preferably, one or more of $R^1$ to $R^3$ is dimethylamino, diethylamino or methylethylamino, optionally substituted with one or more of $SO_3^-$, $PO_3^{2-}$, OH, O-alkyl, SH, S-alkyl, COOH, COO$^-$, ester, amide, halogen, SO-alkyl, $SO_2$-alkyl, $SO_2NH_2$, $SO_2NH$-alkyl, $SO_2N$-dialkyl, and $SO_3$-alkyl, CN, secondary amine or tertiary amine.

In a preferred embodiment, $R^1$ and $R^2$ are each dimethylamino. Alternatively, $R^1$ and $R^2$ may each be optionally substituted methylethylamino.

Preferably, an electron withdrawing substituent is present, and the electron withdrawing substituent is selected from NO, $NO_2$, CN, COOH, ester, COO$^-$, amide, CHO, keto, SO-alkyl, $SO_2$-alkyl, $SO_2NH_2$, $SO_2NH$-alkyl, $SO_2N$-dialkyl, and $SO_3$-alkyl.

Preferably, at least one of $R^{10}$, $R^{11}$, $R^{12}$, $R^{13}$, $R^{14}$ and $R^{15}$ is O-alkyl.

Suitably, one or more pairs of groups $R^4$ and $R^{10}$ and/or $R^5$ and $R^{11}$ and/or $R^6$ and $R^{12}$ and/or $R^7$ and $R^{13}$ and/or $R^8$ and $R^{14}$ and/or $R^9$ and $R^{15}$ is a bridging group consisting of alkylene, O-alkylene, S-alkylene or N-alkylene optionally substituted with one or more of $SO_3^-$, $PO_3^{2-}$, OH, O-alkyl, SH, S-alkyl, COOH, COO$^-$, ester, amide, halogen, SO-alkyl, $SO_2$-alkyl, $SO_2NH_2$, $SO_2NH$-alkyl, $SO_2N$-dialkyl, CN, secondary amine or tertiary amine.

Preferably, $R^{10}$ to $R^{15}$ are each O-methyl or O-ethyl.

Preferably, the reagent further comprises one or more counterions selected from halide, $BF_4^-$, $PF_6^-$, $NO_3^-$, carboxylate, $ClO_4^-$, Li$^+$, Na$^+$, K$^+$, Mg$^{2+}$ and Zn$^{2+}$ so that the reagent is uncharged overall.

Preferably, a linker structure is present, and is formed by reaction of a linker element selected from an active ester, an isothiocyanate, an acid chloride, an aldehyde, an azide, an α-halogenated ketone and an amine with a reaction partner. Suitably, the reaction partner is selected from a polysaccharide, polynucleotide or a protein. Suitably, the linker element is an active ester, and is selected from succinimidyl and pentafluorophenyl active esters.

Suitably, the energy donor is ALEXA FLUOR 594™.

The reagent may be used for in vivo detection of an analyte. For example, the reagent may be contained within a sensor which is implanted into the body. Suitably, the sensor is implanted within the epidermis so that it will be shed from the body over time. Suitable sensor constructions are described in detail in WO02/30275. In this case, it should be possible to illuminate the reagent and measure reagent fluorescence through the layers of the skin above the implanted sensor.

Alternatively, the reagent may be contained within a sensor which is partially implanted within the body but extends outside the body. Such a sensor may take the form of a needle. In this case, the reagent may be illuminated down the bore of the needle and reagent fluorescence may be detected in the same way without light passing through layers of the skin.

The sensor should be permeable to analyte.

In this second aspect, the invention relates to a sensor comprising a semi-permeable membrane enclosing a reagent for use in detecting an analyte as described above.

In a third aspect, the present invention relates to a dye compound having the general formula:

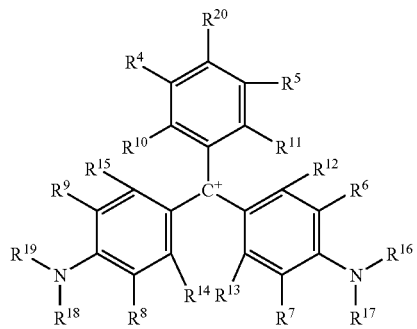

wherein:

$R^4$, $R^5$, $R^6$, $R^7$, $R^8$ and $R^9$ are each independently H, halogen, alkyl, aryl, O-alkyl or S-alkyl and $R^{10}$, $R^{11}$, $R^{12}$, $R^{13}$, $R^{14}$ and $R^{15}$ are each independently hydrogen, O-alkyl, S-alkyl, or alkyl, or one or more pairs of groups $R^{20}$ and $R^4$ and/or $R^{20}$ and $R^5$ and/or $R^4$ and $R^{10}$ and/or $R^5$ and $R^{11}$ and/or $R^6$ and $R^{12}$ and/or $R^7$ and $R^{13}$ and/or $R^8$ and $R^{14}$ and/or $R^9$ and $R^{15}$ is a bridging group consisting of aryl, alkylene, O-alkylene, S-alkylene or N-alkylene optionally substituted with one or more of $SO_3^-$, $PO_3^{2-}$, OH, O-alkyl, SH, S-alkyl, COOH, COO$^-$, ester, amide, halogen, SO-alkyl, $SO_2$-alkyl, $SO_2NH_2$, $SO_2NH$-alkyl, $SO_2N$-dialkyl, $SO_3$-alkyl, CN, secondary amine or tertiary amine, provided that not all of $R^{10}$, $R^{11}$, $R^{12}$, $R^{13}$, $R^{14}$ and $R^{15}$ are hydrogen;

$R^{16}$, $R^{17}$, $R^{18}$ and $R^{19}$ are each independently H, alkyl (preferably $C_1$ to $C_5$ alkyl) or aryl, or one or more of $R^{16}$ and $R^{17}$ or $R^{18}$ and $R^{19}$ is alkylene (preferably $C_3$ to $C_7$ alkylene) optionally substituted with one or more of $SO_3^-$, $PO_3^{2-}$, OH, O-alkyl, SH, S-alkyl, COOH, COO$^-$, ester, amide, halogen, SO-alkyl, $SO_2$-alkyl, $SO_2NH_2$, $SO_2NH$-alkyl, $SO_2N$-dialkyl, $SO_3$-alkyl, CN, secondary amine or tertiary amine;

or one or more of pairs of groups $R^6$ and $R^{16}$, $R^7$ and $R^{17}$, $R^8$ and $R^{18}$ and $R^9$ and $R^{19}$ is alkylene, O-alkylene, S-alkylene or N-alkylene optionally substituted with one or more of $SO_3^-$, $PO_3^{2-}$, OH, O-alkyl, SH, S-alkyl, COOH, COO$^-$, ester, amide, halogen, SO-alkyl, $SO_2$-alkyl, $SO_2NH_2$, $SO_2NH$-alkyl, $SO_2N$-dialkyl, $SO_3$-alkyl, CN, secondary amine or tertiary amine and $R^{20}$ is a linker element selected from an active ester, an isothiocyanate, an acid chloride, an α-halogenated ketone, an azide and an amine.

Suitably, at least one of $R^{10}$, $R^{11}$, $R^{12}$, $R^{13}$, $R^{14}$ and $R^{15}$ is alkyl.

In a preferred embodiment, $R^{16}$, $R^{17}$, $R^{18}$ and $R^{19}$ are each methyl or ethyl. Alternatively, $R^{16}$ and $R^{18}$ may each be methyl and $R^{17}$ and $R^{19}$ may each be ethyl substituted at the 2-position with $SO_3^-$.

Suitably, one or more pairs of groups $R^4$ and $R^{10}$ and/or $R^5$ and $R^{11}$ and/or $R^6$ and $R^{12}$ and/or $R^7$ and $R^{13}$ and/or $R^8$ and $R^{14}$ and/or $R^9$ and $R^{15}$ is a bridging group consisting of alkylene, O-alkylene, S-alkylene or N-alkylene optionally substituted with one or more of $SO_3^-$, $PO_3^{2-}$, OH, O-alkyl, SH, S-alkyl, COOH, COO$^-$, ester, amide, halogen, SO—, $SO_2NH_2$, $SO_2NH$-alkyl, $SO_2N$-dialkyl, CN, secondary amine or tertiary amine.

Preferably, $R^{20}$ is a linker element having the structure:

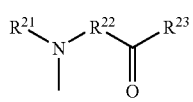

wherein $R^{21}$ is H or alkyl or aryl optionally substituted with one or more of $SO_3^-$, $PO_3^{2-}$, OH, O-alkyl, SH, S-alkyl, COOH, COO⁻, ester, amide, halogen, SO-alkyl, $SO_2N$-dialkyl, CN, secondary amine or tertiary amine and $R^{22}$ is alkylene, O-alkylene, S-alkylene or N-alkylene (preferably $C_2$ to $C_6$) or $R^{21}$ and $R^{22}$ are part of a ring (preferably $C_3$ to $C_7$), optionally substituted with one or more of $SO_3^-$, $PO_3^{2-}$, OH, O-alkyl, SH, S-alkyl, COOH, COO⁻, ester, amide, halogen, SO-alkyl, $SO_2NH_2$, $SO_2NH$-alkyl, $SO_2N$-dialkyl, $SO_3$-alkyl, CN, secondary amine or tertiary amine; and $R^{23}$ is o-succinimidyl, o-pentafluorophenyl, Cl or α-halogenated alkyl.

Preferably, $R^{10}$ to $R^{15}$ are each O-methyl or O-ethyl.

Preferably, the dye compound further comprises one or more counterions selected from halide, $BF_4^-$, $PF_6^-$, $NO_3^-$, carboxylate, $ClO_4^-$, $Li^+$, $Na^+$, $K^+$, $Mg^{2+}$ and $Zn^{2+}$.

In a fourth aspect, the present invention relates to a method of detecting or measuring an analyte using a reagent as described above, comprising the steps of:

contacting the reagent with a sample;

illuminating the reagent and sample with light of wavelength within the absorption spectrum of the energy donor;

detecting non-radiative energy transfer between the energy donor and energy acceptor by measuring the fluorescence of the energy donor; and associating the fluorescence measurements with presence or concentration of analyte.

Suitably, the fluorescence of the energy donor is measured by intensity based or time resolved fluorescence measurements. Preferably, the analyte is measured by comparing sample fluorescence measurements with fluorescence measurements made using known concentrations of analyte.

The light used for illumination preferably has a wavelength above 550 nm.

In a fifth aspect, the present invention relates to a complex of an analyte and a reagent for detecting the analyte wherein the reagent comprises a fluorescent energy donor and an energy acceptor, the energy donor and the energy acceptor being such that when they are sufficiently close to one another energy is non-radiatively transferred from the energy donor following excitation thereof to the energy acceptor quenching fluorescence of the energy donor, wherein the energy acceptor is of the general formula:

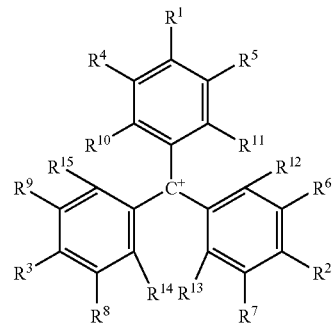

wherein:
$R^1$, $R^2$ and $R^3$ are each independently H, electron donating substituents, or electron withdrawing substituents or $R^3$ is attached to a linker structure, provided that at least two of $R^1$, $R^2$ and $R^3$ are electron donating groups;

$R^4$, $R^5$, $R^6$, $R^7$, $R^8$ and $R^9$ are each independently H, halogen, alkyl, aryl, O-alkyl, S-alkyl and $R^{10}$, $R^{11}$, $R^{12}$, $R^{13}$, $R^{14}$ and $R^{15}$ are each independently hydrogen, O-alkyl, S-alkyl, alkyl, or one or more pairs of groups $R^1$ and $R^4$ and/or $R^1$ and $R^5$ and/or $R^2$ and $R^6$ and/or $R^2$ and $R^7$ and/or $R^3$ and $R^8$ and/or $R^3$ and $R^9$ and/or $R^4$ and $R^{10}$ and/or $R^5$ and $R^{11}$ and/or $R^6$ and $R^{12}$ and/or $R^7$ and $R^{13}$ and/or $R^8$ and $R^{14}$ and/or $R^9$ and $R^{15}$ is a bridging group consisting of aryl, alkylene, O-alkylene, S-alkylene or N-alkylene optionally substituted with one or more of $SO_3^-$, $PO_3^{2-}$, OH, O-alkyl, SH, S-alkyl, COOH, COO⁻, ester, amide, halogen, SO-alkyl, $SO_2$-alkyl, $SO_2NH_2$, $SO_2NH$-alkyl, $SO_2N$-dialkyl, and $SO_3$-alkyl, CN, secondary amine or tertiary amine, provided that not all of $R^{10}$, $R^{11}$, $R^{12}$, $R^{13}$, $R^{14}$ and $R^{15}$ are hydrogen; and wherein the presence of the analyte modulates the distance between the energy donor and the energy acceptor.

The invention will be further described with reference to preferred embodiments illustrated by the Examples, and as illustrated in FIG. 1, which shows a glucose dose-response curve, and FIG. 2, which shows normalised absorption and emission spectra of ALEXA FLUOR 594™ and HMCV-1-dextran in aqueous PBS buffer 50 mM, pH=7.4 (Exitation of AF594 at 570 nm in a 0.7 μM solution).

EXAMPLE

Preparation of Dye Compound 4

Synthetic Methods and Materials

Figure 1:
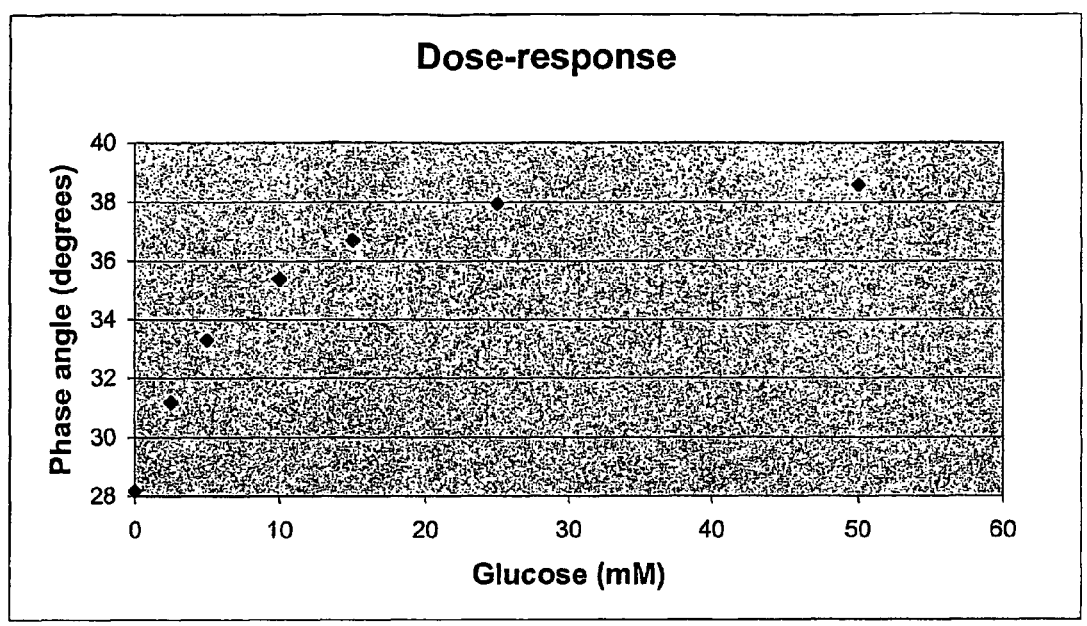
FIG. 1 shows a glucose response curve.

All reagents used were standard grade unless otherwise mentioned. Ether and THF were dried by distillation from sodium/benzophenone under nitrogen. Benzene was dried by standing over sodium. NMR spectra were on a 250 or 400 MHz spectrometer. FABMS spectra were obtained using 1,4-dicyanobutane as matrix.

Elemental analysis was done at the University of Copenhagen, Department of Chemistry, Elemental Analysis Laboratory, Universitetsparken 5, 2100 Copenhagen, Denmark.

Tris(2,4,6-trimethoxyphenyl)carbenium Tetrafluoroborate (1-BF₄). A solution of phenyllithium was prepared by addition of bromobenzene (24.5 g, 156 mmol) in dry ether (50 mL) to lithium wire (2.30 g, 328 mmol) in dry ether (100 mL). 1,3,5-Trimethoxy-benzene (25.1 g, 149 mmol) in dry benzene (100 mL) was added, and the reaction mixture was stirred at room temperature under argon for 70 h. Diethyl carbonate (5.30 g, 45 mmol) in dry benzene (150 mL) was added, and the reaction mixture was refluxed for 3 days. The cooled reaction mixture was poured into NaOH solution (300 mL, 1 M). The phases were separated, and the water phase was extracted with ether. The combined organic phases were dried over MgSO₄ and filtered yielding a clear yellow solution. Addition of aqueous HBF₄ solution (12 mL, 50% approximately 100 mmol) resulted in immediate precipitation of the deep blue carbenium salt. The dark purple precipitate was filtered off, washed thoroughly with dry ether, and dried over solid KOH to yield 26.0 g (96%) of the crude product. Reprecipitation by addition of water to an acetonitrile solution followed by recrystallisation from methanol gave the pure compound in 70% overall yield. $^1$H NMR (250 MHz, CDCl₃); δ 6.05 (6H,s), 3.99 (9H,s), 3.59 (18H,s). $^{13}$C NMR (400 MHz, CDCl₃): δ 169.70, 166.47, 163.93, 118.62, 91.53, 56.52, 56.36. MS (FAB⁺): m/z 513 (M⁺). UV-vis $\lambda_{max}$ (nm (log ε)) (CH₂Cl₂): 584 (4.55), 467 (3.98), 322 (3.68), 287 (4.02). Anal. Cacd for C₂₈H₃₃O₉BF₄: C, 56.01; H, 5.50. Found: C, 55.69; H, 5.64.

Tris(2,4,6-trimethoxyphenyl)carbenium Chloride (1-Cl). This compound was prepared analogously to 1-BF₄ (starting with 15.0 g of 1,3,5-trimethoxybenzene). Instead of HBF₄, gaseous HCl was bubbled through the hydrolysed and dried reaction mixture. The dark purple crystalline precipitate was filtered off, washed thoroughly with dry ether, and dried over solid KOH to yield 10.1 g (66%) of the crude product. The MS (FAB⁺), $^1$H NMR, and $^{13}$C NMR spectra were identical with those of the BF₄ salt.

Synthesis of HMCV-1:

Scheme 1.

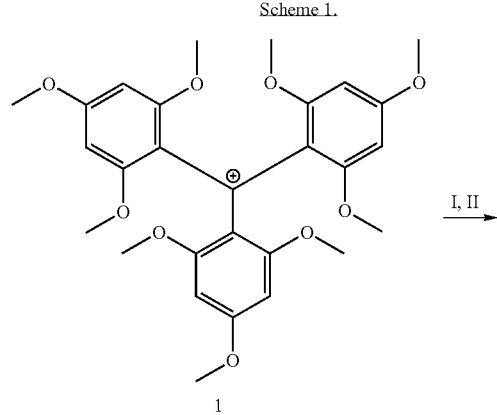

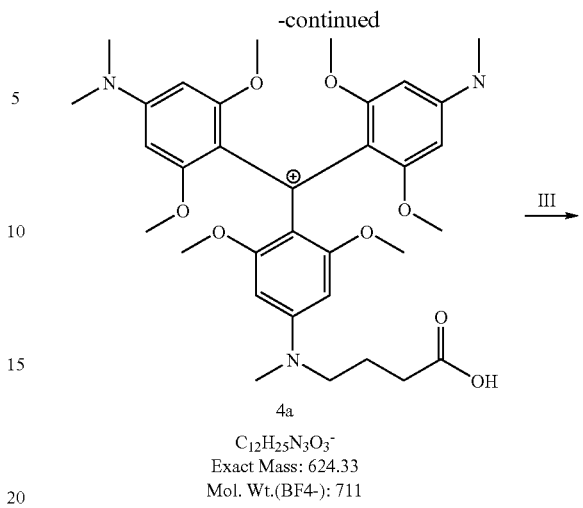

4a
C₁₂H₂₅N₃O₃⁻
Exact Mass: 624.33
Mol. Wt.(BF4-): 711

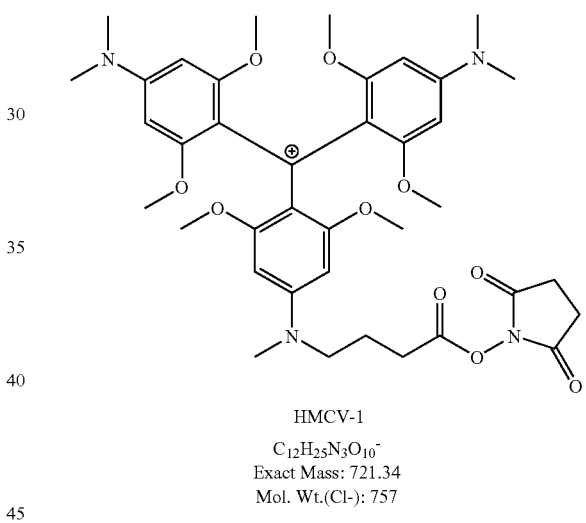

HMCV-1
C₁₂H₂₅N₃O₁₀⁻
Exact Mass: 721.34
Mol. Wt.(Cl-): 757

I) 4-(N-methylamino)-butanic acid hydrochloride (1 eq.), Diisopropylethylamine, in acetonitrile, 20° C., 20 hours. II) Dimethylamine (excess). III) TSTU, Diisopropylethylamine, in acetonitrile, 20° C., 2 hours.

4a (BF₄⁻): 4-(methylamino)butyric acid hydrochloride (1.36 g; 8.8 mmol), 1 (5.0 g; 8.3 mmol), and diisopropylethylamine (5 mL) was dissolved in acetonitrile (120 mL). The reaction mixture was stirred at 30-35° C. in a dry nitrogen atmosphere for 22 h. Aqueous dimethylamine (40 mL of a 40% solution) was added and the reaction mixture was stirred for four more days. Solvent and excess dimethylamine were removed in vacuo and the remaining material dissolved in chloroform. The chloroform solution was washed twice with brine and dried over MgSO₄ before evaporation of the solvent and reprecipitation of the product from CH₂Cl₂/ether. Yield: 4.4 g (70%) of a dark blue powder.

MS (FAB₊): m/z 624 (M+)

$^1$H-NMR (400 MHz, DMSO-d₆) δ 8.34. (1H, bs), 6.03 (2H, s), 5.83 (4H, s), 3.49 (2H, m), 3.46 (6H, s), 3.44 (12H, s), 3.12 (3H, s (masked)), 3.08 (12H, s), 1.94 (2H, t), 1.70 (2H, m).

HMCV-1 (Cl⁻): TSTU (2-succinimido-1,1,3,3-tetramethyluronium tetrafluoroborate; 0.8 g, 2.6 mmol) was added to a solution of 4a (0.9 g, 1.26 mmol) and diisopropylethylamine (0.55 g, 4.5 mmol) in acetonitrile (15 mL). The reaction mixture was stirred in a closed flask for 2 h, before it was poured into an ice-cold nearly sat. NaCl solution (approx. 150 mL) acidified with HCl-aq (4 mL, 2 M). The water phase was extracted with chloroform (2×150 mL). The combined chloroform phases was washed with brine (2×50 mL) and dried over MgSO$_4$. Evaporation of the solvent and reprecipitation from CH$_2$Cl$_2$/ether gave a dark blue powder (0.80 g, 84%).

MS (FAB+): m/z 721 (M+)

$^1$H-NMR $^1$H-NMR br.(400 MHz, DMSO-d$_6$): δ 5.88 (2H, s), 5.85 (4H,s), 3.60 (2H, s), 3.46 (12H, s), 3.45 (6H, s), 3.15 (12H, s), 3.12 (3H, s), 2.85 (4H, s), 2.80 (2H, t), 1.95 (2H, m).

Synthesis of HMCV-2:

Scheme 2.

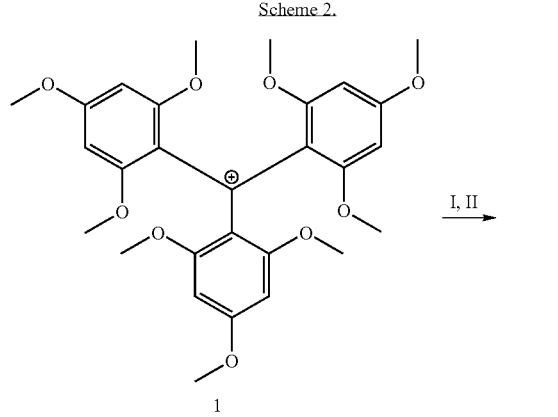

1

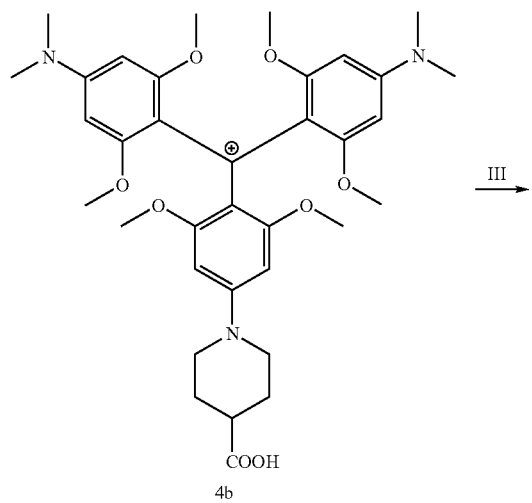

4b

C$_{35}$H$_{46}$N$_3$O$_3^+$
Exact Mass: 636.33
Mol. Wt.(PF6): 782

-continued

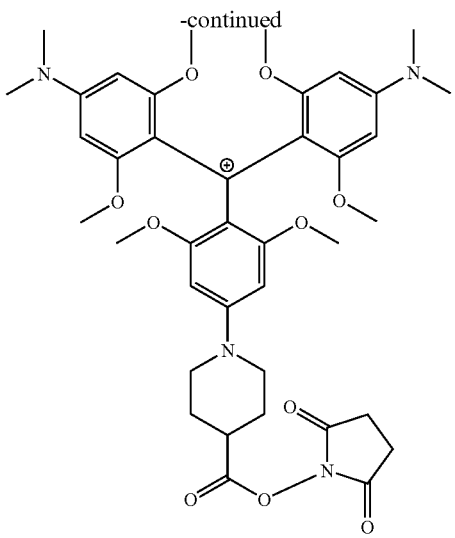

HMCV-2

C$_{42}$H$_{25}$N$_4$O$_{10}^+$
Exact Mass: 733.34
Mol. Wt.(PF6): 880

I) Piperidine-4-carboxylic acid (1 eq.), Diisopropylethylamine, in NMP, 80° C. II) Dimethylamine (excess), 20° C. III) TSTU, Diisopropylethylamine, in acetonitrile, 20° C., 2 hours.

4b (PF$_6^-$): A suspension of piperidine-4-carboxylic acid (Isonipecotic acid) (0.215 g; 1.7 mmol) and diisopropylethylamine (1 mL) in NMP (N-methyl-2-pyrrolidone, 20 mL) was added to a solution of 1 (1.0 g; 1.7 mmol) in 30 mL of NMP. The reaction mixture was heated in an 80-100° C. warm oil bath for 2 h (until the reaction mixture was bright red) and left at room temperature overnight. Dimethylamine (10 mL of a 33% solution in absolute ethanol) was added and the reaction mixture was stirred for another 24 h at room temperature. The reaction mixture was poured into an aqueous KPF$_6$ solution (400 mL, 0.2 M) and HCl-aq (2M) was added in small portions until precipitation. The blue precipitate was filtered off and washed with pure water, dried, dissolved in DCM, filtered and reprecipitated by addition of ether. Yield: 0.85 g of a dark blue powder (64%).

MS (FAB+): m/z 636 (M+)

$^1$H-NMR (CD$_3$CN, int. solvent ref. 1.94 ppm): δ 6.03 (2H, s), 5.81 (4H, s), 3.90 (2H, m), 3.48 (12H, s), 3.47 (6H, s), 3.14 (12H, s), 3.04 (2H, m), 2.61 (1H, m), 2.15 (1H, br), 1.97 (2H, m), 1.71 (2H, m).

HMCV-2 (PF$_6^-$): TSTU (2-succinimido-1,1,3,3-tetramethyluronium tetrafluoroborate; 0.72 g, 2.4 mmol) was added to a solution of 4b (0.8 g, 1 mmol) and diisopropylethylamine (0.47 g) in acetonitrile (15 mL). The reaction mixture was stirred in a closed flask for 2 h, before it was poured into an cold NaCl solution (ca 100 mL) acidified with HCl-aq (4 mL, 2 M solution, ca 4 mmol). The water phase was extracted with chloroform (2×100 mL). The combined chloroform phases were washed with brine (2×50 mL) and dried over MgSO$_4$. Filter aid (10 g) was added to the filtered chloroform phase and the solvent removed. Workup by column chromatography (silica, CHCl$_3$/MeCN 5:1) gave, after evaporation of the solvent (the first blue fraction was collected) and re-precipitation from CH$_2$Cl$_2$/ether a dark blue powder (0.55 g, 62%).

MS (FAB+): m/z 732 (M+)

$^1$H-NMR (DMSO, int. solvent ref 2.50 ppm): δ 6.08 (2H, s), 5.84 (4H, s), 4.93 (2H, m), 3.45 (12H, s), 3.44 (6H, s), 3.14

(12H, s), 3.14 (2H, m (masked)), 2.82 (4H), 2.03 (2H, m), 1.74 (2H, m). (CDCl$_3$, int. solvent ref 7.76 ppm) δ 5.94 (2H, s), 5.70 (4H, s), 3.80 (2H, m), 3.53 (12H, s), 3.18 (6H), 3.16 (2H, m (masked)), 2.97 (1H, m), 2.85 (4H, s), 2.19 (2H, m), 2.04 (2H, m).

Synthesis of HMCV-3:

Synthesis of the HMCV-3 precursor 4c has been accomplished by two synthetic routes. A: by a "one-pot" procedure analogous to the one used in the synthesis of HMCV-1 and HMCV-2, where the linker carrying amino group (4-(N-methylamino)-butanic acid) is introduced first, followed by the two sulfonic acid substituted amino functions (N-methyltaurine) (Scheme 3). In method B the sequence is reversed and performed in two steps with isolation of the double substituted product 3c (Scheme 4).

Scheme 3 (Method A):

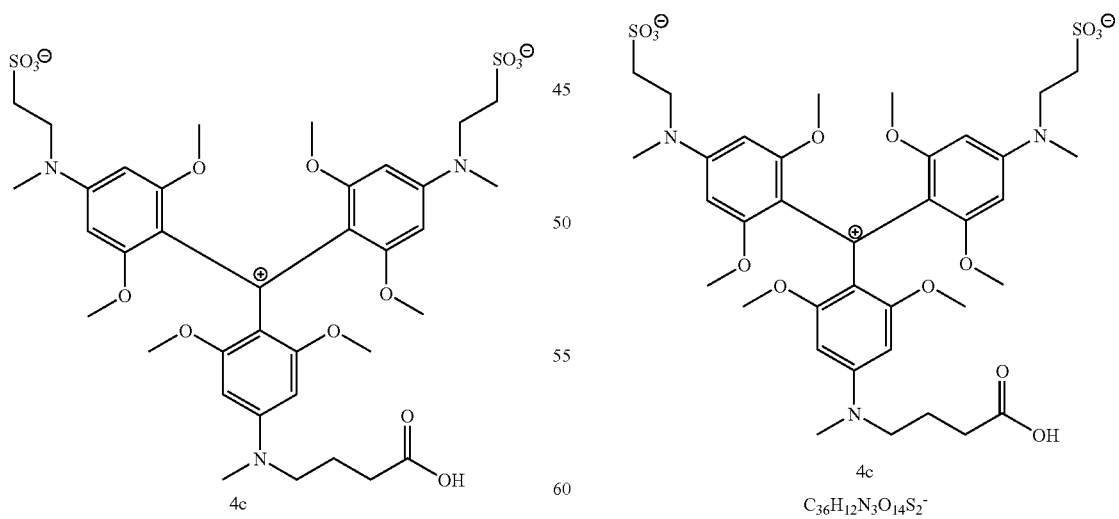

4c
C$_{36}$H$_{25}$N$_3$O$_{14}$S$_2$
Exact Mass: 810.26
Mol. Wt.(Na+): 833

I) 4-(N-methylamino)-butanic acid hydrochloride (1 eq.), Diisopropylethylamine, in DMSO, 20° C., 24 hours. II) sodium N-methyltaurine (excess), 70° C., 48 hours.

Scheme 4 (Method B):

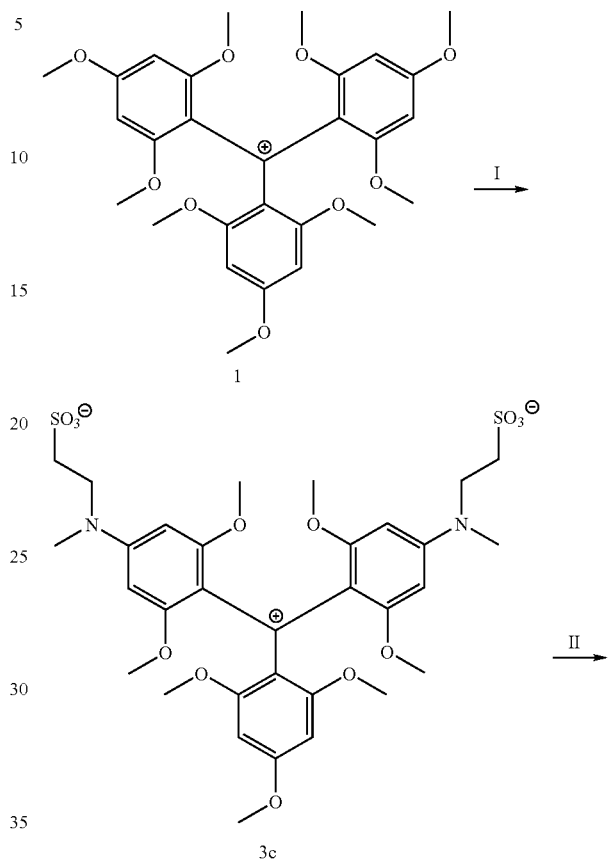

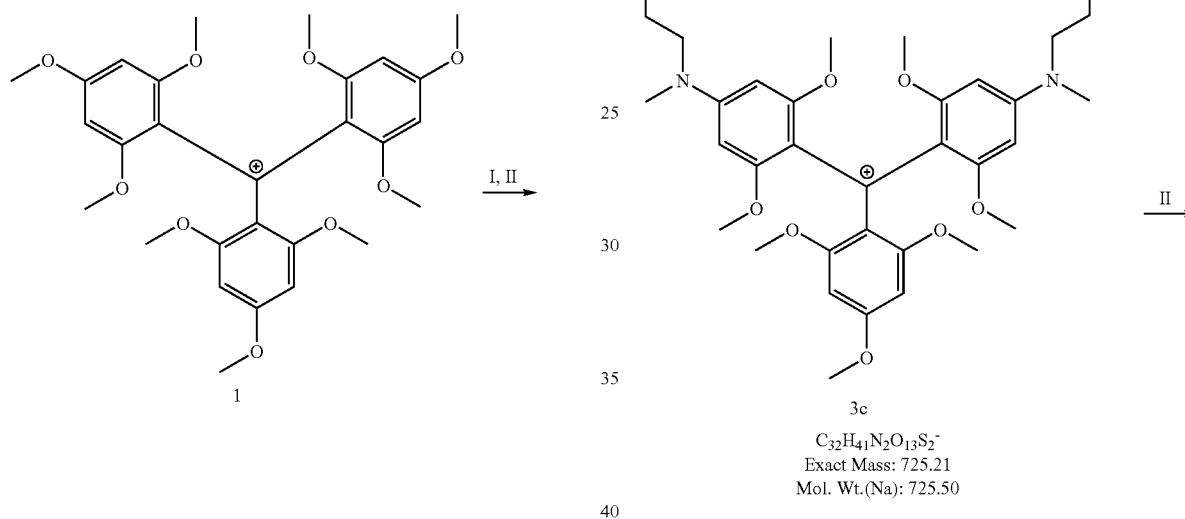

3c
C$_{32}$H$_{41}$N$_2$O$_{13}$S$_2^-$
Exact Mass: 725.21
Mol. Wt.(Na): 725.50

4c
C$_{36}$H$_{12}$N$_3$O$_{14}$S$_2^-$
Exact Mass: 810.26
Mol. Wt.(Na+): 833

I) sodium N-methyltaurine (excess), 20° C., 3 days. II) 4-(N-methylamino)-butanic acid hydrochloride (excess), Na$_2$CO$_3$, in DMSO, 70° C., 3 days.

4c (Na+) (method A): A solution of 4-(methylamino)butyric acid hydrochloride (0.275 g; 1.8 mmol), 1 (1.0 g; 1.7 mmol), and diisopropylethylamine (1 mL) in DMSO (25 mL) was stirred for 20 h. at room temperature before sodium N-methyltaurine (2.0 g, 12 mmol), diisopropylethylamine (1 mL) and DMSO (20 mL) was added. The reaction mixture was then stirred for two days at about 70° C. and two days at room temperature. The reaction mixture was filtered through silica followed by thoroughly washing with methanol. The blue filtrate was concentrated and the crude product precipitated, as a sticky blue wax, by addition of ethyl acetate. Column chromatography (silica, MeCN/MeOH 5:2) gave a blue solid (first blue fraction/band), which was further purified by dissolution in hot ethanol followed by filtration (hot). After cooling the ethanol solution was filtered again and the precipitate was washed with ethanol (leaving a white material). The blue ethanol solution was evaporated yielding 0.3 g of 4c (18%).

MS (FAB+, Glycerol): m/z 812 ($MH_2^+$), 834 ($MNaH^+$), 856 ($MNa_2^+$)

$^1$H-NMR ($CD_3OD$, int. solvent ref 3.35 ppm): δ 5.98 (6H, s), 3.95 (4H, t), 3.62 (2H, t), 3.57 (6H, s), 3.56 (12H, s), 3.21 (3H, s), 3.20 (6H, s), 3.15 (4H, t), 2.41 (2H, t), 1.99 (2H, m).

4c by Method B:

3c (Na+): A solution of sodium N-methyltaurine (1.3 g, 8 mmol), and 1 (1.0 g; 1.7 mmol) in DMSO (25 mL) was stirred for three days at room temperature. Addition of ethyl acetate (approx. 500 mL) gave a blue precipitate (and a red mother liquor). The solid material was heated to reflux in absolute ethanol (approx. 150 mL) and left overnight at room temperature. The precipitate was filtered off, dissolved in methanol and filtered through silica (5 cm layer), which was washed with methanol. Evaporation of the solvent and re-precipitation from methanol/ethyl acetate yielded a blue powder (1.1 g, 88%).

MS (FAB+, Glycerol): m/z 727 ($MH_2^+$), 749 ($MNaH^+$), 765 ($MNaK^+$), 771 ($MNa_2^+$)

$^1$H-NMR ($CD_3OD$, int. solvent ref 3.35 ppm): δ 6.20 (2H, s), 5.98 (4H, s), 4.00 (4H, t), 3.87 (3H, s), 3.58 (12H, s), 3.56 (6H, s), 3.28 (6H, s), 3.17 (2H, t).

4c (Na+): A solution of 3c (0.5 g; 0.67 mmol), 4-(N-methylamino)-butanic acid hydrochloride (0.5 g, 3.26 mmol), and dry $Na_2CO_3$ (0.5 g) in DMSO (7 mL) was stirred for 3 days at 70° C. The crude product was precipitated from the cooled reaction mixture by addition of ethyl acetate, giving a sticky blue material (ca 1.1 g.). Column chromatography (silica, MeCN/MeOH 5:2) gave the product 4c as a blue solid after evaporation of the solvents (0.25 g, 44%).

MS (FAB+, Glycerol): m/z 812 ($MH_2^+$)

$^1$H-NMR ($CD_3OD$, int. solvent ref 3.35 ppm): δ 5.98 (6H, s), 3.95 (4H, t), 3.62 (2H, t), 3.57 (6H, s), 3.56 (12H, s), 3.21 (3H, s), 3.20 (6H, s), 3.15 (4H, t), 2.41 (2H, t), 1.99 (2H, m).

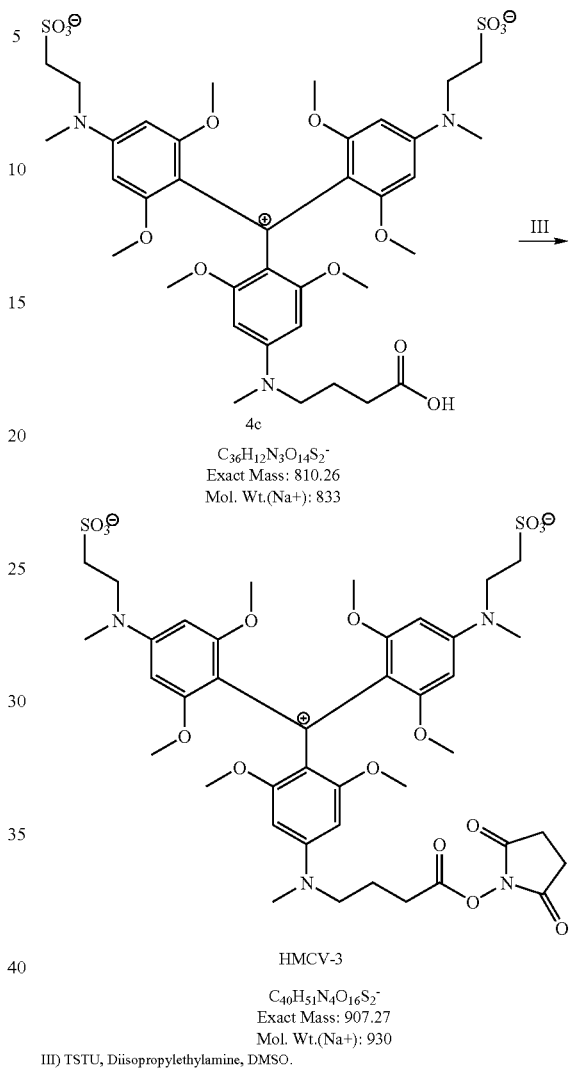

Scheme 5.

III) TSTU, Diisopropylethylamine, DMSO.

HMCV-3 (Na+): TSTU (2-succinimido-1,1,3,3-tetramethyluronium tetrafluoroborate; 0.20 g, 0.6 mmol) was added to a solution of 4c (0.25 g, 0.3 mmol) and diisopropylethylamine (0.06 g) in dry DMSO (10 mL). The reaction mixture was stirred in a closed flask for 2 h, before the crude product was precipitated by addition of ethyl acetate. The sticky blue material was washed from the filter with methanol and dried at high vacuum. Workup by column chromatography (silica, $H_2O$/MeCN 1:10) gave, after evaporation of the solvent (high vacuum at room temperature) and re-precipitation from methanol/ethyl acetate a dark blue powder (0.25 g, 90%).

MS (FAB+, Glycerol): m/z 909 ($MH_2^+$), 931 ($MNaH^+$), 947 ($MKH^+$), $^1$H-NMR($CD_3OD$, int. solvent ref 3.35 ppm): δ 5.99 (4H, s), 5.94 (2H, s), 3.95 (4H, t), 3.68 (2H, t), 3.57 (12H, s), 3.58 (2H, masked), 3.55 (6H, s), 3.21 (9H, s), 3.16 (4H, t), 2.88 (4H, s), 2.80 (2H,s), 2.13 (2H, m).

Attachment of HMCV-1 to Aminodextran

Aminodextran (130 mg, Mw 110.000, 0.5 mmol $NH_2$/g dextran) was dissolved in 6.5 mL aqueous sodium carbonate (15 mM, pH=8.5 to give a solution with dextran concentration 182 µM, 20 mg/mL). To 3.0 mL of this solution under stirring was added HMCV-1 (5.65 mg in 200 µL DMSO) in 10 µL portions over 10 minutes. The solution was stirred at room temperature for 1 hour and dialysed. (3 mL dialysis slide, 12-14.000 MwCO membrane) extensively against an aqueous phosphate buffer (10 mM $H_2PO_4^-/HPO_4^{2-}$, 4 mM $K^+$, 145 mM $Na^+$, 0.1 mM $Ca^{2+}$, 0.1 mM $Mn^{2+}$, pH=7.4). The concentration of labeled dextran was determined from the dilution during dialysis. The degree of labelling (the DOL-value) was determined from a series of UV-Vis spectra of the resulting solution (3.2 mL, concentration of dextran 168 µM, DOL=10).

Attachment of ALEXA FLUOR 594™ to Concanavalin A (ConA)

A solution of ConA (Type III, Sigma) was made as follows. Methyl-α-D-mannopyranoside (0.97 g), 30 µL aqueous $CaCl_2$ (0.1 M) and 30 µL aqueous $MnCl_2$ (0.1 M) were mixed in 20 mL 0.5 M $Na_2CO_3$ buffer (pH=8.5). Then ConA (1.00 g~150 mg protein) was added and the suspension stirred vigorously for 1 h. The solution was centrifuged and the supernatant collected.

To 13.0 mL of this solution was added ALEXA FLUOR 594™ (10.0 mg in 800 mL dry DMSO) in 20 µL portions over 10 min. The resulting blue solution was stirred for 1 h and then succinic anhydride (18.2 mg in 867 µL dry DMSO) was added in 20 µL portions over 10 min. The solution was stirred for another 1.5 h after which it was transferred to a 15 mL dialysis slide and dialysed against the same buffer as described for the HMCV-1-Dextran synthesis. To the buffer was added 2 mM $NaN_3$ to prevent growth. (15.4 mL, concentration of protein dimer 59 µM, DOL=4.0)

Use of Analyte Binding Reagent Labelled with Dye Compound 4 in FRET Assay

The glucose measurement assay chemistry of the preferred embodiment is based on the competition between binding of dextran and glucose to Concanavalin A (Con A) as discussed above.

Con A is labelled with ALEXA FLUOR 594™ (AF594) (donor) And dextran is labelled with a non-fluorescent dye, HMCV-1 (acceptor), absorbing within the emission band of AF594.

The fluorescence lifetime is measured by frequency-domain fluorimetry. The intensity of the excitation light is modulated causing the excited donor to emit light modulated with the same frequency and delayed by the lifetime of the excited state. This results in a phase shift between the excitation light and the emitted fluorescence.

We chose AF594-labelled (ConA) as the sugar binding lectin and the HMCV-1 labelled dextran as a glucose analogue. The bulk concentrations of the donor and acceptor dyes used, [AF594] and [HMCV-1] were constant during the whole experiment and their ratio was 1:6. This is consistent with the Förster theory condition that the donor concentration is much smaller than the acceptor concentration. [Ref.: O. J. Rolinski, D. J. S. Birch, L. J. McCartney, J. C. Pickup, J. Photochem. Photobiol. B: Biol. 54, 26-34, 2000] It is our finding that the Förster theory is best fulfilled when ConA is labelled with the donor and the poly-sugar dextran is labelled with the acceptor.

Measurements

The donor conjugate, the acceptor conjugate and the PBS-buffer (50 mM PBS-buffer, pH=7.4, ionic strength adjusted to 150 mM with NaCl) were mixed so that the final concentration in the assay chemistry of ConA was 20 µM and the concentration of dextran was 50 µM. The molar ratio ([ConA]/[Dex]) was 0.40 and the concentration ratio ([AF594]/[HMCV-1]) was 0.16. Two hollow cellulose fibres (Spectrum Laboratories, Inc., regenerated cellulose, fibre outer diameter 216 µm, fibre inner diameter 200 µm, MWCO 13 kDa Reorder No. 132294) were filled with assay chemistry, and were then mounted in a custom-made holder placed in a fluorescence cell containing PBS-buffer.

The phase excitation shift was measured using a phase and modulation fluorimeter (Koala from ISS, Inc., Champaign, Ill.). The light source was a yellow LED. A XF1067 band pass filter, which transmits light from 540 to 590 nm (Glenn Spectra Ltd) was placed in the excitation channel as well as in the reference channel. The emission channel was fitted with a XF3061 band pass filter, which transmits light from 610 to 690 nm (Glenn Spectra Ltd).

The glucose dose-response was measured by successive replacement of the PBS buffer with PBS buffer containing increasing glucose concentration from 0 mM to 50 mM glucose.

The results are shown in Table 1 and in FIG. 1.

TABLE 1

| Glucose (mM) | Phase angle (degree) |
|---|---|
| 0 | 28.2 |
| 2.5 | 31.2 |
| 5 | 33.3 |
| 10 | 35.4 |
| 15 | 36.7 |
| 25 | 38.0 |
| 50 | 38.6 |

The above assay system was tested in vivo in a clamped pig experiment. The assay was loaded in a hollow fiber which by a needle was placed in the subcutus of the skin. The results from the phase measurements showed a slight phase shift compared with the in vitro experiment but could be correlated very well with reference values for whole blood glucose.

The acceptors of the preferred embodiment of the present invention have a number of advantages over known acceptors.

Figure 2:
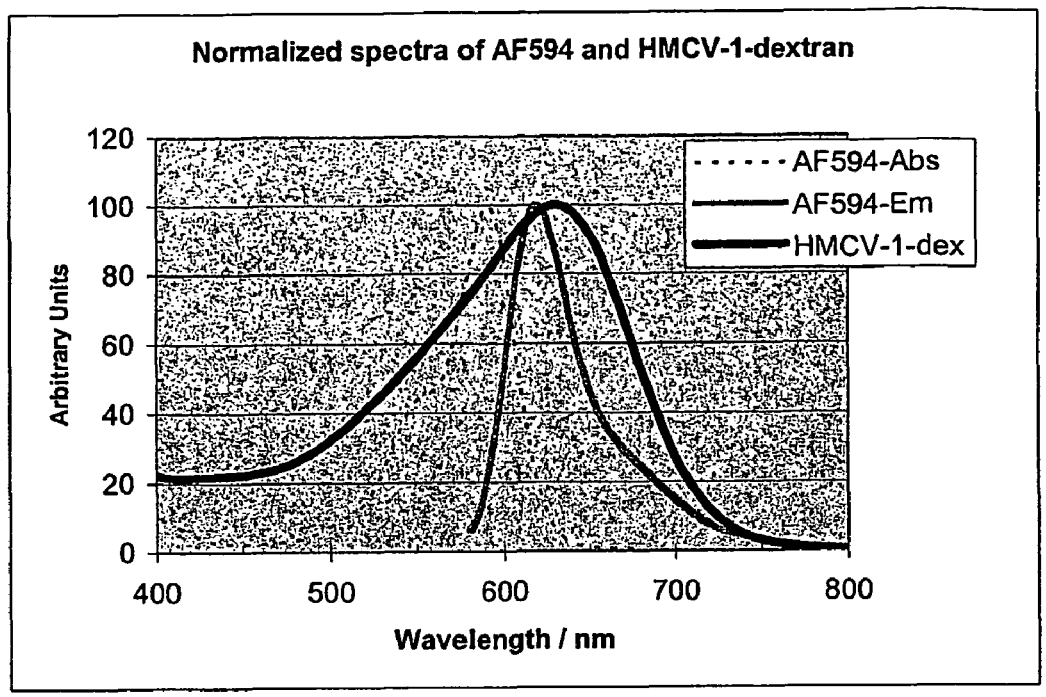
FIG. 2 shows a normalized spectrum of AF594 and HCMCV-1-dextran.

First, the HMCV acceptors have a broad and intense absorption spectrum (550 to 700 nm). This means that they can be used with a variety of donors (See FIG. 2).

Second, the acceptors absorb at high wavelengths. This means that they are suitable for in vivo use at wavelengths where autofluorescence does not interfere with the measurements.

Third, the center carbon atom of the dyes is shielded by ortho substituents on the aromatic moities prohibiting degradation processes that initiates by either reductive, oxidative or nucleophilic attack at this position.

Fourth, the absorption spectrum of the acceptors is not significantly affected by conjugation to analyte or analyte binding reagent. This means that the performance of the acceptors is predictable.

Fifth, the acceptors do not fluoresce and will not contribute to background fluorescence signal.

The invention claimed is:

1. A reagent for use in detecting an analyte, comprising a fluorescent energy donor, an energy acceptor and optionally a counterion, the energy donor and the energy acceptor being such that when they are sufficiently close to one another energy is non-radiatively transferred from the energy donor following excitation thereof to the energy acceptor quenching fluorescence of the energy donor, wherein the energy acceptor is of the formula:

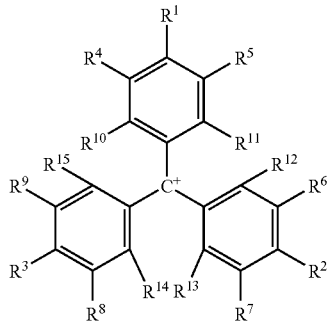

wherein:
R¹, R² and R³ are each independently H, electron donating substituents, or electron withdrawing substituents or R³ is attached to a linker structure, provided that at least two of R¹, R² and R³ are electron donating groups;
R⁴, R⁵, R⁶, R⁷, R⁸ and R⁹ are each independently H, halogen, alkyl, aryl, O-alkyl, S-alkyl and R¹⁰, R¹¹, R¹², R¹³, R¹⁴ and R¹⁵ are each independently hydrogen, O-alkyl, S-alkyl, alkyl, or one or more pairs of groups R¹ and R⁴ and/or R¹ and R⁵ and/or R² and R⁶ and/or R² and R⁷ and/or R³ and R⁸ and/or R³ and R⁹ and/or R⁴ and R¹⁰ and/or R⁵ and R¹¹ and/or R⁶ and R¹² and/or R⁷ and R¹³ and/or R⁸ and R¹⁴ and/or R⁹ and R¹⁵ is a bridging group consisting of aryl, alkylene, O-alkylene, S-alkylene or N-alkylene optionally substituted with one or more of SO₃⁻, PO₃²⁻, OH, O-alkyl, SH, S-alkyl, COOH, COO⁻, ester, amide, halogen, SO-alkyl, SO₂-alkyl, SO₂NH₂, SO₂NH-alkyl, SO₂N-dialkyl, SO₃-alkyl, CN, secondary amine or tertiary amine, provided that not all of R¹⁰, R¹¹, R¹², R¹³, R¹⁴ and R¹⁵ are hydrogen and at least one of R¹⁰, R¹¹, R¹², R¹³, R¹⁴ and R¹⁵ is O-alkyl;
and wherein the distance between the energy donor and the energy acceptor of the reagent is capable of modulation by a suitable analyte to be detected.

2. A reagent as claimed in claim 1, wherein the energy donor and energy acceptor are linked together by a covalent linkage.

3. A reagent as claimed in claim 2, wherein the covalent linkage between the energy donor and energy acceptor is cleavable to increase the distance between the energy donor and the energy acceptor of the reagent.

4. A reagent as claimed in claim 2, wherein the energy donor and energy acceptor are linked via a polynucleotide sequence or a polynucleotide analogue sequence or a polypeptide sequence, the sequence having a conformation which is capable of modulation by a suitable analyte to be detected so as to modulate the distance between the energy donor and the energy acceptor of the reagent.

5. A reagent as claimed in claim 1, wherein the energy donor and energy acceptor are linked together by non-covalent binding.

6. A reagent as claimed in claim 5 wherein the non-covalent binding exists between an analyte binding agent linked to one of the energy donor and the energy acceptor and an analyte analogue linked to the other of the energy donor and the energy acceptor, the non-covalent binding being disruptable by a suitable analyte so as to increase the distance between the energy donor and the energy acceptor of the reagent.

7. A reagent as claimed in claim 6, wherein the analyte binding agent is a lectin.

8. A reagent as claimed in claim 6, wherein the analyte analogue is a glucose analogue.

9. A reagent as claimed in claim 8, wherein the analyte analogue is dextran.

10. A reagent as claimed in claim 1, wherein a linker structure is attached to the energy acceptor at R³, or where a bridging group is present optionally the linker structure is attached to the energy acceptor at the bridging group.

11. A reagent as claimed in claim 1, wherein the electron donating substituents are selected from amino, primary amine, secondary amine, O-alkyl, alkyl, S-alkyl, amide, ester, OH and SH.

12. A reagent as claimed in claim 11, wherein one or more of R¹ to R³ is dimethylamino, diethylamino or methylethylamino, any of those groups being optionally substituted with one or more of SO₃⁻, PO₃²⁻, OH, O-alkyl, SH, S-alkyl, COOH, COO⁻, ester, amide, halogen, SO-alkyl, SO₂-alkyl, SO₂NH₂, SO₂NH-alkyl, SO₂N-dialkyl, SO₃-alkyl, CN, secondary amine or tertiary amine.

13. A reagent as claimed in claim 1, wherein an electron withdrawing substituent is present, and the electron withdrawing substituent is selected from NO, NO₂, CN, COOH, ester, COO⁻, amide, CHO, keto, SO-alkyl, SO₂-alkyl, SO₂NH₂, SO₂NH-alkyl, SO₂N-dialkyl, and SO₃-alkyl.

14. A reagent as claimed in claim 1, wherein one or more pairs of groups R⁴ and R¹⁰ and/or R⁵ and R¹¹ and/or R⁶ and R¹² and/or R⁷ and R¹³ and/or R⁸ and R¹⁴ and/or R⁹ and R¹⁵ is a bridging group consisting of alkylene, O-alkylene, S-alkylene or N-alkylene optionally substituted with one or more of SO₃⁻, PO₃²⁻, OH, O-alkyl, SH, S-alkyl, COOH, COO⁻, ester, amide, halogen, SO-alkyl, SO₂-alkyl, SO₂NH₂, SO₂NH-alkyl, SO₂N-dialkyl, SO₃-alkyl, CN, secondary amine or tertiary amine.

15. A reagent as claimed in claim 1, wherein R¹⁰ to R¹⁵ are each O-methyl or O-ethyl.

16. A reagent as claimed in claim 1, further comprising one or more counterions selected from halide, BF₄⁻, PF₆⁻, NO₃⁻, carboxylate, ClO₄⁻, Li⁺, Na⁺, K⁺, Mg²⁺ and Zn²⁺.

17. A reagent as claimed in claim 1, wherein a linker structure is present, and is formed by reaction of a linker element selected from an active ester, an isothiocyanate, an acid chloride, an aldehyde, an azide, an a-halogenated ketone and an amine with a reaction partner.

18. A reagent as claimed in claim 17, wherein the reaction partner is selected from a polysaccharide, a polynucleotide and a protein.

19. A reagent as claimed in claim 17, wherein the linker element is an active ester, and is selected from succinimidyl and pentafluorophenyl active esters.

20. A reagent as claimed in claim 1, wherein the energy donor is a dye that absorbs at 594 nm and fluoresces at 620 nm.

21. A reagent as claimed in claim 1, in which:
R¹ and R² are both NMe₂ or both MeNCH₂CH₂SO₃⁻
R³ is a linker element which is a succinimidyl ester
R⁴⁻⁹ are all H
R¹⁰⁻¹⁵ are all OMe;
the energy donor and energy acceptor are linked together by non-covalent binding which exists between an analyte binding agent linked to one of the energy donor and the energy acceptor and an analyte analogue linked to the other of the energy donor and the energy acceptor, the non-covalent binding being disruptable by the analyte so as to increase the distance between the energy donor and the energy acceptor of the reagent.

22. A reagent as claimed in claim 21, wherein the analyte is glucose.

23. A reagent as claimed in claim 22, wherein the analyte analogue is dextran.

24. A reagent as claimed in claim 22, wherein the analyte binding agent is a lectin.

25. A reagent as claimed in claim 21, wherein the energy donor is a dye that absorbs at 594 nm and fluoresces at 620 nm.

26. A method of detecting or measuring an analyte with a reagent as claimed in claim 1, comprising the steps of:
contacting the reagent with a sample;
illuminating the reagent and sample with light of wavelength within the absorption spectrum of the fluorescent energy donor;
detecting non-radiative energy transfer between the energy donor and energy acceptor by measuring the fluorescence of the energy donor; and
correlating the fluorescence measurements with the presence or concentration of the analyte.

27. A method as claimed in claim 26, wherein the fluorescence of the energy donor is measured by making intensity based or time resolved fluorescence measurements.

28. A method as claimed in claim 26, wherein the analyte is measured by comparing sample fluorescence measurements with fluorescence measurements made using known concentrations of analyte.

29. A dye compound having the formula:

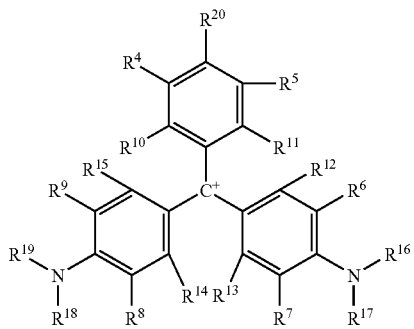

wherein:
$R^4$, $R^5$, $R^6$, $R^7$, $R^8$ and $R^9$ are each independently H, halogen, alkyl, aryl, O-alkyl or S-alkyl and $R^{10}$, $R^{11}$, $R^{12}$, $R^{13}$, $R^{14}$ and $R^{15}$ are each independently hydrogen, O-alkyl, S-alkyl, or alkyl, or one or more pairs of groups $R^4$ and $R^{10}$ and/or $R^5$ and $R^{11}$ and/or $R^6$ and $R^{12}$ and/or $R^7$ and $R^{13}$ and/or $R^8$ and $R^{14}$ and/or $R^9$ and $R^{15}$ is a bridging group consisting of aryl, alkylene, O-alkylene, S-alkylene or N-alkylene optionally substituted with one or more of $SO_3^-$, $PO_3^{2-}$, OH, O-alkyl, SH, S-alkyl, COOH, COO$^-$, ester, amide, halogen, SO-alkyl, $SO_2$-alkyl, $SO_2NH_2$, $SO_2NH$-alkyl, $SO_2N$-dialkyl, $SO_3$-alkyl, CN, secondary amine or tertiary amine, provided that not all of $R^{10}$, $R^{11}$, $R^{12}$, $R^{13}$, $R^{14}$ and $R^{15}$ are hydrogen; $R^{16}$, $R^{17}$, $R^{18}$ and $R^{19}$ are each independently H, alkyl or aryl, or one or more of $R^{16}$ and $R^{17}$ or $R^{18}$ and $R^{19}$ is alkylene, optionally substituted with one or more of $SO_3^{31}$, $PO_3^{2-}$, OH, O-alkyl, SH, S-alkyl, COOH, COO$^-$, ester, amide, halogen, SO-alkyl, $SO_2$-alkyl, $SO_2NH_2$, $SO_2NH$-alkyl, $SO_2N$-dialkyl, $SO_3$-alkyl, CN, secondary amine or tertiary amine; or one or more of pairs of groups $R^6$ and $R^{16}$, $R^{17}$ and $R^{17}$, $R^8$ and $R^{18}$, and $R^9$ and $R^{19}$ is alkylene, O-alkylene, S-alkylene or N-alkylene optionally substituted with one or more of $SO_3^-$, $PO_3^{2-}$, OH, O-alkyl, SH, S-alkyl, COOH, COO$^-$, ester, amide, halogen, SO-alkyl, $SO_2$-alkyl, $SO_2NH_2$, $SO_2NH$-alkyl, $SO_2N$-dialkyl, $SO_3$-alkyl, CN, secondary amine or tertiary amine
and
$R^{20}$ is a linker element selected from the group consisting of an active ester, an isothiocyanate, an acid chloride, an a-halogenated ketone, an azide and an amine of the formula:

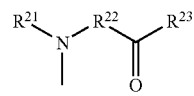

$R^{21}$ is H or alkyl or aryl optionally substituted with one or more of $SO_3^-$, $PO_3^{2-}$, OH, O-alkyl, SH, S-alkyl, COOH, COO$^-$, ester, amide, halogen, SO-alkyl, $SO_2N$-dialkyl, CN, secondary amine or tertiary amine and $R^{22}$ is alkylene, O-alkylene, S-alkylene or N-alkylene or $R^{21}$ and $R^{22}$ are part of a ring, optionally substituted with one or more of $SO_3^-$, $PO_3^{2-}$, OH, O-alkyl, SH, S-alkyl, COOH, COO$^-$, ester, amide, halogen, SO-alkyl, $SO_2NH_2$, $SO_2NH$-alkyl, $SO_2N$-dialkyl, $SO_3$-alkyl, CN, secondary amine or tertiary amine and
$R^{23}$ is o-succinimidyl, o-pentafluorophenyl, CI or α-halogenated alkyl; and optionally comprising a counterion.

30. A dye compound as claimed in claim 29, wherein at least one of $R^{10}$, $R^{11}$, $R^{12}$, $R^{13}$, $R^{14}$ and $R^{15}$ is alkyl.

31. A dye compound as claimed in claim 30, wherein one or more pairs of groups $R^4$ and $R^{10}$ and/or $R^5$ and $R^{11}$ and/or $R^6$ and $R^{12}$ and/or $R^7$ and $R^{13}$ and/or $R^8$ and $R^{14}$ and/or $R^9$ and $R^{15}$ is a bridging group consisting of alkylene, O-alkylene, S-alkylene or N-alkylene optionally substituted with one or more of $SO_3$, $PO_3^{2-}$, OH, O-alkyl, SH, S-alkyl, COOH, COO$^{31}$, ester, amide, halogen, SO-alkyl, $SO_2NH_2$, $SO_2NH$-alkyl, $SO_2N$-dialkyl, $SO_3$-alkyl, CN, secondary amine or tertiary amine.

32. A dye compound as claimed in claim 29, wherein $R^{10}$ to $R^{15}$ are each O-methyl or O-ethyl.

33. A dye compound as claimed in claim 29, further comprising one or more counterions selected from halide, $BF_4^-$, $PF_6^-$, $NO_3^-$, carboxylate, $ClO_4^-$, Li$^+$, Na$^+$, K$^+$, Mg$^{2+}$ and Zn$^{2+}$.

* * * * *